(12) United States Patent
Choi et al.

(10) Patent No.: US 7,488,684 B2
(45) Date of Patent: Feb. 10, 2009

(54) ORGANIC ALUMINUM PRECURSOR AND METHOD OF FORMING A METAL WIRE USING THE SAME

(75) Inventors: Jung-Sik Choi, Seongnam-si (KR); Jung-Ho Lee, Seongnam-si (KR); Jun-Hyun Cho, Suwon-si (KR); Youn-Joung Cho, Suwon-si (KR); Tae-Sung Kim, Suwon-si (KR); Mi-Ae Kim, Seoul (KR); Kyoo-Chul Cho, Yongin-si (KR); Dong-Jun Lee, Seoul (KR)

(73) Assignee: Samsung Electronics Co., Ltd., Suwon-si, Gyeonggi-do (KR)

( * ) Notice: Subject to any disclaimer, the term of this patent is extended or adjusted under 35 U.S.C. 154(b) by 0 days.

(21) Appl. No.: 11/523,604

(22) Filed: Sep. 20, 2006

(65) Prior Publication Data

US 2007/0066061 A1 Mar. 22, 2007

(30) Foreign Application Priority Data

Sep. 21, 2005 (KR) .................. 10-2005-0087508

(51) Int. Cl.
*H01L 21/285* (2006.01)
(52) U.S. Cl. .............. 438/688; 438/585; 438/597; 257/E21.17

(58) Field of Classification Search ............. 438/585, 438/597, 688; 257/E21.17
See application file for complete search history.

(56) References Cited

U.S. PATENT DOCUMENTS

| 6,130,160 | A | 10/2000 | Vaartstra | |
|---|---|---|---|---|
| 2004/0026786 | A1* | 2/2004 | Leu et al. | .................. 257/758 |
| 2006/0257567 | A1 | 11/2006 | Peters et al. | |

FOREIGN PATENT DOCUMENTS

| JP | 2003-034868 | 2/2003 |
|---|---|---|
| JP | 2000-086673 | 3/2003 |
| JP | 2004-323943 | 11/2004 |
| KR | 100246155 B1 | 12/1999 |
| KR | 100292687 B1 | 3/2001 |
| KR | 1020000022650 A | 4/2005 |

OTHER PUBLICATIONS

John A Glass Jr., "Chemical Vapor Deposition Precursor Chemistry. Formation of Pure Aluminum, Alumina, and Aluminum Boride Thin Films from Boron-Containing Precursor Compounds by Chemical Vapor Deposition," Chem. Mater. 1992, 4, 530-538.

* cited by examiner

*Primary Examiner*—George Fourson
(74) *Attorney, Agent, or Firm*—Volentine & Whitt, PLLC

(57) ABSTRACT

An organic aluminum precursor includes aluminum as a central metal, and borohydride and trimethylamine as ligands. In a method of forming an aluminum layer or wire, the organic aluminum presursor is introduced onto a substrate, and then thermally decomposed. The aluminum decomposed from the organic aluminum precursor is deposited on the substrate.

8 Claims, 5 Drawing Sheets

ORGANIC ALUMINUM PRECURSOR AND METHOD OF FORMING A METAL WIRE USING THE SAME

BACKGROUND OF THE INVENTION

1. Field of the Invention

Example embodiments of the present invention relate to an organic aluminum precursor and to a method of forming a metal wire using the same. More particularly, example embodiments of the present invention relate to an organic aluminum precursor used for a chemical vapor deposition (CVD) process or a cyclic CVD process and to a method of forming a metal wire using the organic aluminum precursor.

A claim of priority under 35 USC § 119 is made to Korean Patent Application NO. 2005-87508 filed on Sep. 21, 2005, the contents of which are herein incorporated by references in their entirety.

2. Description of the Related Art

In order to fabricate a high speed and large capacity semiconductor device, it is necessary that metal conductive structures that transmit electric signals in the semiconductor device have favorable electrical characteristics.

The metal conductive structures in the semiconductor device are usually formed of aluminum (Al), tungsten (W) or copper (Cu). Aluminum has a lower specific resistance relative to that of tungsten. In addition, an aluminum layer pattern may be formed by a dry etching process unlike a copper layer pattern. Thus, aluminum is widely used to form a conductive structure such as a contact, a plug and a wire.

An aluminum wire is usually formed by a plasma vapor deposition (PVD) process such as a sputtering process. However, as an aspect ratio of a via or a contact hole increases, the formation of the aluminum wire by the PVD process has reached its limit.

As a result, a chemical vapor deposition (CVD) process has been applied to form an aluminum wire. A precursor used in a CVD process includes, for example, trimethyl aluminum (TMA), dimethyl aluminum hydride (DMAH) or triisobutyl aluminum (TIBA).

The above-mentioned precursors have a high vapor pressure, which is consider advantageous because the precursor may be easily deposited by a CVD process. However, the CVD process requires a high temperature of about 250° C. to about 400° C. In addition, the aluminum wire may include impurities such as carbon, thereby increasing an electric resistance.

In order to avoid these problems, a deposition process using a dimethylethyl amine alane (DMEAA) precursor has been studied. The DMEM precursor has a high vapor pressure and is deposited at a temperature of about 100° C. to about 200° C. However, the DMEAA precursor is thermally unstable at a room temperature. Hence, a deposition process using a more stable methyl pirolidine alane (MPA) precursor has been suggested. A method of forming an aluminum wire using the MPA precursor is disclosed in Korean Laid-Open Patent Publication No. 2000-0022650. Although the MPA precursor is more thermally stable than the DMEAA precursor, the MPA precursor is also thermally and chemically unstable at a temperature above about 30° C. Hence, when the MPA precursor is introduced into a chamber by a CVD process, the MPA precursor may remain as particles in the chamber and fall on the aluminum wire during formation of the aluminum wire or after formation of the aluminum wire.

SUMMARY OF THE INVENTION

According to one aspect of the present invention, there is provided an organic aluminum precursor. The organic aluminum precursor is used for forming an aluminum wire or an aluminum layer and includes aluminum as a central metal, and borohydride and trimethylamine as ligands.

In an example embodiment of the present invention, a chemical structure of the organic aluminum precursor is in accordance with the formula:

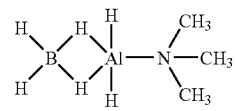

According to another aspect of the present invention, there is provided a method of forming a metal wire. In the method, an organic aluminum precursor including aluminum as a central metal, and borohydride and trimethylamine as ligands, is introduced onto a substrate. The organic aluminum precursor is then thermally decomposed, and aluminum decomposed from the organic aluminum precursor is deposited on the substrate.

According to still another aspect of the present invention, there is provided a method of forming a metal wire. In the method, an insulation layer pattern including an opening is formed on a substrate, where the opening exposes a conductive pattern included in the substrate thereon. A chemical vapor deposition (CVD) process is performed using an organic aluminum precursor including aluminum as a central metal, and borohydride and trimethylamine as ligands, is performed to form a first aluminum layer on inner walls of the opening and on an upper surface of the insulation layer pattern. A physical vapor deposition (PVD) process is performed to form a second aluminum layer on the first aluminum layer.

BRIEF DESCRIPTION OF THE DRAWINGS

The above and other features and advantages of the present invention will become readily apparent from the detailed description that follows, with reference to the accompanying drawings, in which.

DETAILED DESCRIPTION OF EMBODIMENTS

Figure 1:
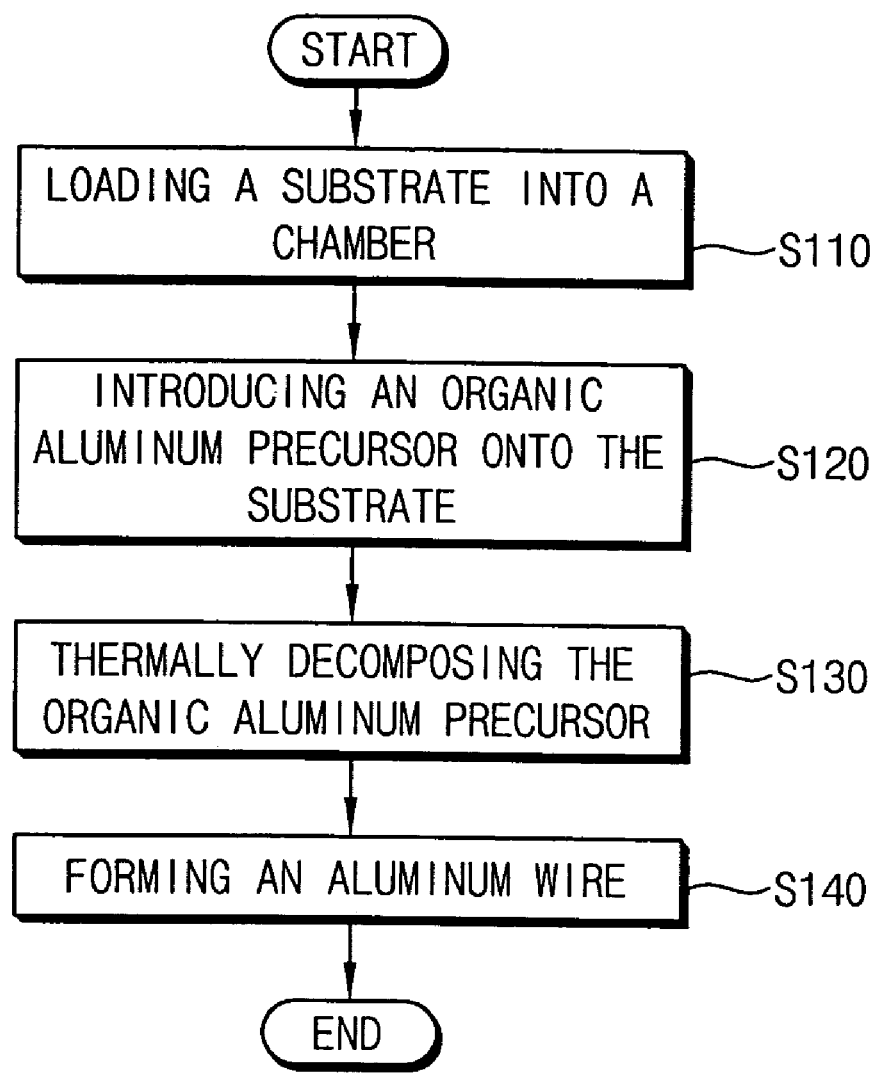
FIG. 1 is a flow chart for describing a method of forming an aluminum wire in accordance with an example embodiment of the present invention.

The present invention is described more fully hereinafter with reference to the accompanying drawings, in which example embodiments of the present invention are shown. The present invention may, however, be embodied in many different forms and should not be construed as limited to the example embodiments set forth herein. Rather, these embodiments are provided so that this disclosure will be thorough and complete, and will fully convey the scope of the present invention to those skilled in the art. In the drawings, the sizes and relative sizes of layers and regions may be exaggerated for clarity.

It will be understood that when an element or layer is referred to as being "on," "connected to" or "coupled to" another element or layer, it can be directly on, connected or coupled to the other element or layer or intervening elements or layers may be present. In contrast, when an element is referred to as being "directly on," "directly connected to" or "directly coupled to" another element or layer, there are no intervening elements or layers present. Like reference numerals refer to like elements throughout. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

The terminology used herein is for the purpose of describing particular embodiments only and is not intended to be limiting of the present invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Example embodiments of the present invention are described herein with reference to cross-sectional illustrations that are schematic illustrations of idealized embodiments (and intermediate structures) of the present invention. As such, variations from the shapes of the illustrations as a result, for example, of manufacturing techniques and/or tolerances, are to be expected. Thus, example embodiments of the present invention should not be construed as limited to the particular shapes of regions illustrated herein but are to include deviations in shapes that result, for example, from manufacturing. For example, an implanted region illustrated as a rectangle will, typically, have rounded or curved features and/or a gradient of implant concentration at its edges rather than a binary change from implanted to non-implanted region. Likewise, a buried region formed by implantation may result in some implantation in the region between the buried region and the surface through which the implantation takes place. Thus, the regions illustrated in the figures are schematic in nature and their shapes are not intended to illustrate the actual shape of a region of a device and are not intended to limit the scope of the present invention.

Unless otherwise defined, all terms (including technical and scientific terms) used herein have the same meaning as commonly understood by one of ordinary skill in the art to which the present invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Organic Aluminum Precursor

An organic aluminum precursor of the present invention may be used for forming an aluminum layer or an aluminum wire. The organic aluminum precursor may exhibit an improved evaporation at a low temperature.

The organic aluminum precursor includes aluminum as a central metal and two kinds of ligands linked with the central metal. Examples of the ligands may include borohydride and trimethylamine. Thus, the organic aluminum precursor may include an aluminum borohydride trimethylamine (ABHTMA) precursor having the following formula.

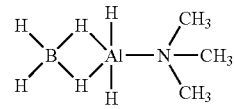

The organic aluminum precursor may be used in a chemical vapor deposition (CVD) process or a cyclic CVD process for forming an aluminum layer or an aluminum wire.

The ABHTMA precursor may have a higher evaporability than that of a conventional organic aluminum precursor such as a methyl pirolidine alane (MPA) precursor at an equal temperature. The ABHTMA precursor may exist in a stable vapor phase at a room temperature in a chamber used for performing the CVD process. The ABHTMA precursor may be preferably vaporized at a temperature of about 20° C. to about 50° C. More preferably, the ABHTMA precursor may be vaporized at a temperature of about 30° C. to about 40° C.

In one example embodiment of the present invention, the ABHTMA precursor may be vaporized at a temperature of about 30° C., and preferably have a vapor pressure of about 0.4 Torr to about 0.6 Torr, more preferably, a vapor pressure of about 0.45 Torr to about 0.55 Torr. In another example embodiment of the present invention, the ABHTMA precursor may be vaporized at a temperature of about 50° C., and preferably have a vapor pressure of about 1.2 Torr to about 1.4 Torr. More preferably, the ABHTMA precursor may have a vapor pressure of about 1.25 Torr to about 1.35 Torr.

The ABHTMA precursor may be thermally decomposed at a temperature of about 80° C. to about 200° C., thereby possibly removing ligands from the central metal. A high temperature above about 200° C. is not required for a thermal decomposition of the ABHTMA precursor. Thus, when an aluminum wire is formed on a substrate using the ABHTMA precursor, a thermal stress of lower structures included in the substrate due to a high processing temperature may be prevented or reduced.

When an aluminum wire is formed by a CVD process using the organic aluminum precursor such as the ABHTMA precursor having the above properties, the organic aluminum precursor may not be thermally decomposed before being introduced into a chamber. This is because the organic aluminum precursor is thermally stable. Thus, defects of the aluminum wire may be prevented or reduced. In addition, a chamber cleaning process need not be frequently performed so that a throughput in a manufacturing process of the semiconductor device may be improved.

Preparation of an Organic Aluminum Precursor

EXAMPLE

About 453.32 g of $AlCl_3$ diluted in about 2 L of ether, and about 180.63 g of $LiAlH_4$ diluted in about 1.5 L of ether, were each prepared at a temperature of about −30° C. The $AlCl_3$ solution was dropped into the $LiAlH_4$ solution at a temperature of about −30° C. About 401.91 g of an $N(CH_3)_3$ gas of was further added to initiate a reaction for about 5 hours. As a result, a $ClAlH_2N(CH_3)_3$ solution was synthesized. The $ClAlH_2N(CH_3)_3$ solution was filtered, and a solvent was removed from the $ClAlH_2N(CH_3)_3$ solution. About 514.44 g of $NaBH_4$ was diluted in about 2 L of ether in a flask, and the filtered $ClAlH_2N(CH_3)_3$ solution was added into the $NaBH_4$ solution for about 30 minutes. After a reaction for about 20 hours, a mixed solution of the $ClAlH_2N(CH_3)_3$ solution and the $NaBH_4$ solution was filtered. A solvent was removed from the mixed solution and then a remaining compound was purified by a vacuum distillation. As a result, aluminum borohydride trimethylamine as colorless liquid product was obtained.

Method of Forming an Aluminum Wire

FIG. 1 is a flow chart illustrating a method of forming an aluminum wire in accordance with an example embodiment of the present invention.

Referring to FIG. 1, a substrate is loaded into a chamber for a CVD process in step S110.

The substrate may be supported by a susceptor in the chamber. The chamber may be set up to have a pressure and a temperature that is appropriate for performing the CVD process.

When an inner pressure of the chamber is less than about 0.001 Torr, the reactivity between aluminum and the substrate may be reduced. When the inner pressure of the chamber is more than about 10 Torr, a process may not be readily controlled. Thus, the chamber may preferably have an inner pressure of about 0.001 Torr to about 10 Torr. More preferably, the chamber may have an inner pressure of about 0.05 Torr to about 5 Torr.

In one example embodiment of the present invention, the chamber may have a temperature of about 20° C. to about 50° C. In another example embodiment of the present invention, the chamber may have a temperature of about 30° C. to about 40° C.

An aluminum borohydride trimethylamine (ABHTMA) precursor as an organic aluminum precursor is introduced onto the substrate in the chamber in step S120.

The ABHTMA precursor may have a higher evaporability than that of a methyl pirolidine alane (MPA) precursor, which is a conventional organic aluminum precursor. When the ABHTMA precursor is introduced into the chamber for forming an aluminum wire, the ABHTMA precursor may not be thermally decomposed in advance because the ABHTMA precursor may be thermally stable at a room temperature. Thus, a generation of aluminum particles may be prevented or reduced.

The organic aluminum precursor may be introduced into the chamber in a gas phase by a liquid delivery system (LDS), a bubbling system, etc. In addition, the organic aluminum precursor may be introduced into the chamber in a vapor phase with a carrier gas. Examples of the carrier gas may include an inert gas such as an argon (Ar) gas, a helium (He) gas, a nitrogen ($N_2$) gas, or a neon (Ne) gas. These can be used individually or in a mixture of two or more thereof.

The organic aluminum precursor introduced onto the substrate is thermally decomposed in step S130.

The organic aluminum precursor is introduced onto the substrate in a gas phase and then the organic aluminum precursor is thermally decomposed when an appropriate temperature condition is established. The substrate may be supported by a susceptor. The ligands are removed from aluminum of the organic aluminum precursor by a thermal decomposition. In one example embodiment of the present invention, the substrate or the chamber for forming an aluminum wire may have a temperature of about 80° C. to about 200° C. In another example embodiment of the present invention, the substrate or the chamber for forming the aluminum wire may have a temperature of about 80° C. to about 160° C. For example, a temperature of the substrate or the chamber is in a range of about 140° C. to about 160° C.

The organic aluminum precursor of the present invention may be thermally decomposed at a temperature of less than about 200° C. Thus, when the aluminum wire is formed using the organic aluminum precursor of the present invention, lower structures included in the substrate may be prevented from having a thermal stress due to a high temperature.

The aluminum wire is formed on the substrate by depositing aluminum (Al) decomposed from the organic aluminum precursor in step S140.

Aluminum decomposed from the organic aluminum precursor is continuously chemisorbed on the substrate, and an aluminum wire is formed on the substrate by the continuously chemisorbing aluminum. The aluminum wire may have a crystalline orientation of <1, 1, 1> that may be advantageous to prevent an electro migration.

In one example embodiment of the present invention, the aluminum wire may be formed by a CVD process. In another example embodiment of the present invention, the aluminum wire may be formed by a cyclic CVD process.

Method of Manufacturing a Semiconductor Device

FIGS. 2 to 6 are cross-sectional views for describing a method of manufacturing an aluminum wire of a semiconductor device in accordance with an example embodiment of the present invention.

Figure 2:
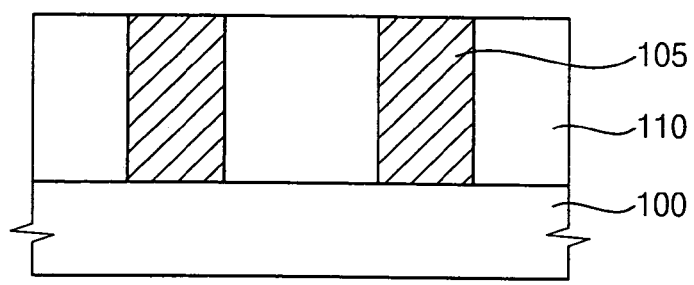
FIGS. 2 to 6 are cross-sectional views for describing a method of forming an aluminum wire of a semiconductor device in accordance with an example embodiment of the present invention.

FIG. 2 is a cross-sectional view illustrating a process of forming a first insulating interlayer pattern.

Referring to FIG. 2, a first insulating interlayer pattern 110 is formed on a substrate 100. The first insulating interlayer pattern 110 includes a contact 105 therein. The contact 105 is formed through the first insulating interlayer pattern 110 and is electrically connected to the substrate 100. The substrate 100 may include lower structures (not shown) thereon. The lower structures may include, for example, a bit line, a word line, a gate structure, a pad, a plug, and/or a metal wiring.

To form the first insulating interlayer pattern 110, a first insulating interlayer is formed on the substrate 100 to cover the lower structures. The first insulating interlayer may be formed, for example, using an oxide such as boro phosphor silicate glass (BPSG), phosphor silicate glass (PSG), undoped silicate glass (USG), spin on glass (SOG), plasma enhanced tetraethyl orthosilicate (PE-TEOS), or high density plasma-chemical vapor deposition (HDP-CVD) oxide. A contact hole is formed in the first insulating interlayer to expose the lower structures. The first insulating interlayer is patterned to form the first insulating interlayer pattern 110.

To form the contact 105, a conductive layer is formed on the first insulating interlayer pattern 110 to fill the contact hole. The conductive layer may be formed using a metal such as aluminum (Al). The conductive layer is partially removed by a chemical mechanical polishing (CMP) process or an etch back process or a combination of CMP and etch back to expose the first insulating interlayer pattern 110. Hence, the contact 105 is formed in the first insulating interlayer pattern 110.

Figure 3:
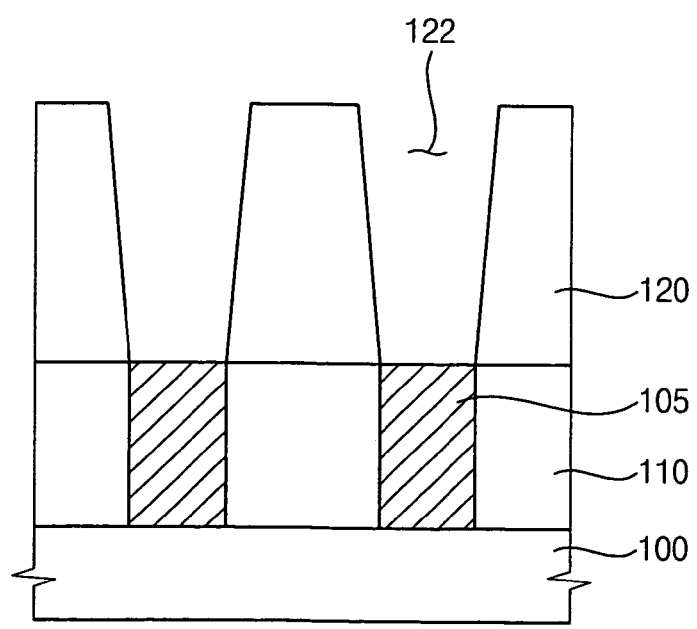

FIG. 3 is a cross-sectional view for describing a process of forming a second insulating interlayer pattern having an opening.

Referring to FIG. 3, a second insulating interlayer pattern 120 is formed on the contact 105 and the first insulating interlayer pattern 110. The second insulating interlayer pattern 120 includes an opening 122 exposing the contact 105.

To form the second insulating interlayer pattern 120, a second insulating interlayer is formed on the contact 105 and the first insulating interlayer pattern 110. In one example embodiment of the present invention, the second insulating interlayer may be formed, for example, using an oxide such as BPSG, PSG, USG, SOG, PE-TEOS, or HDP-CVD oxide. In another example embodiment of the present invention, the second insulating interlayer may be formed using a doped oxide having a dielectric constant of less than about 3.5. Examples of the doped oxide having the dielectric constant of less than about 3.5 may include such as carbon-doped oxide (SiOC), hydrogen silsesquioxane (HSQ, SiOH), or methyl silsesquioxane (MSQ, $SiOCH_3$).

For example, the second insulating interlayer may be formed by spin-coating and baking hydrogen silsesquioxane. Then, the formation of a parasitic capacitor between the lower structures and a metal wire may be prevented or reduced.

A mask pattern (not shown) is formed on the second insulating interlayer. The second insulating interlayer exposed by the mask pattern is selectively etched to form an opening 122 exposing the contact 105. In this manner, the second insulating interlayer is patterned to form the second insulating interlayer pattern 120. Then, the mask pattern is removed from the second insulating interlayer pattern 120. When the mask pattern is a photoresist pattern, the mask pattern may be removed by a plasma ashing process and a cleaning process.

In one example embodiment of the present invention, before forming the second insulating interlayer, an etch stop layer (not shown) may be further formed on the contact 105 and the first insulating interlayer pattern 110. The etch stop layer may prevent or reduce etching damage to the contact 105, which can occur in an etching process for forming the opening 122 in the second insulating interlayer. The etch stop layer may be formed to have a thickness of about 10 Å to about 150 Å. Also, the etch stop layer may be formed using a nitride or a metal oxide having an etching selectivity relative to the second insulating interlayer. The etch stop layer on the contact 105 may be removed by a wet etching process after forming the opening 122 in the second insulating interlayer.

Figure 4:
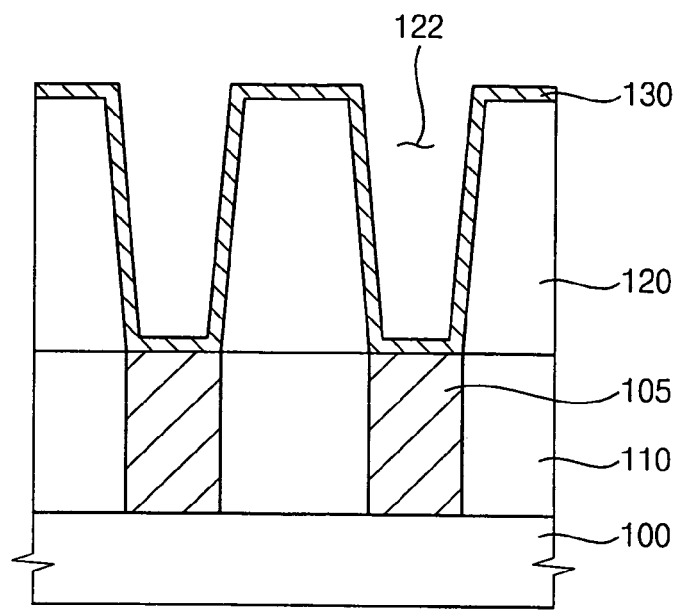

FIG. 4 is a cross-sectional view for describing a process of forming a barrier metal layer.

Referring to FIG. 4, a barrier metal layer 130 is conformably formed on a bottom and sidewalls of the opening 122, and on the second insulating interlayer pattern 120. The barrier metal layer 130, which does not fill the opening 122, may be formed to have a substantially uniform thickness.

The barrier metal layer 130 may serve to prevent or reduce aluminum in an aluminum wire formed on the barrier metal layer 130 from diffusing into the second insulating interlayer pattern 120. The barrier metal layer 130 may have a good adhesive characteristic and a low contact resistance. In addition, the barrier metal layer 130 may be highly resistant to a thermal stress and a mechanical stress. In one example embodiment of the present invention, the barrier metal layer 130 may be formed in a single-layered structure of a titanium (Ti) layer or a titanium nitride (TiN) layer. In another example embodiment of the present invention, the barrier metal layer 130 may be formed in a multi-layered structure of a titanium/titanium nitride (Ti/TiN) layer. For example, the barrier metal layer 130 is formed using titanium. When the barrier metal layer 130 is formed using titanium, the barrier metal layer 130 may effectively prevent or reduce a metal from diffusing into the second insulating interlayer pattern 120 and may have a good electrical conductivity.

In one example embodiment of the present invention, the barrier metal layer 130 may be formed using titanium to have a thickness of about 100 Å to about 500 Å. When a thickness of the barrier metal layer 130 is above about 500 Å, a contact resistance with the contact 105 may increase. When the thickness of the barrier metal layer 130 is below about 100 Å, the diffusion of a metal and the generation of particles may not be effectively prevented. Therefore, the thickness of the barrier metal layer 130 may preferably be in a range of about 100 Å to about 500 Å.

Figure 5:
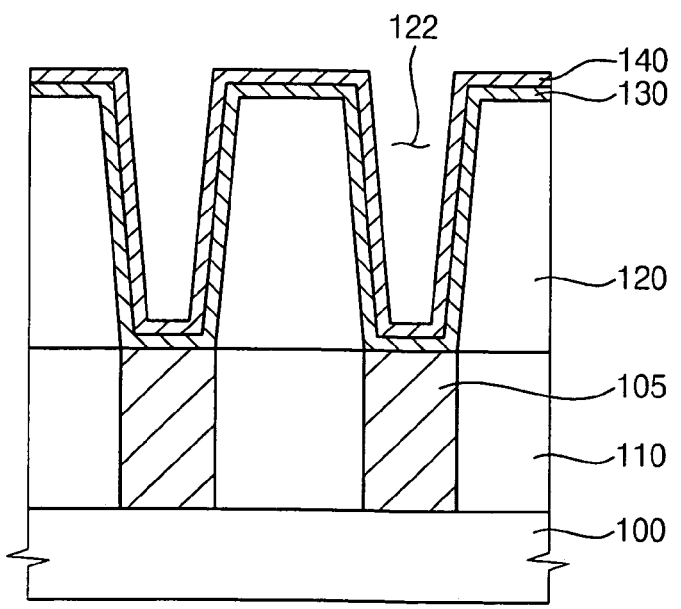

FIG. 5 is a cross-sectional view for explaining a process of forming a first aluminum layer.

Referring to FIG. 5, a first aluminum layer 140 is formed on the barrier metal layer 130. The first aluminum layer 140 may be formed by a CVD process using an organic aluminum precursor according to embodiments of the present invention. The first aluminum layer 140 may serve as a seed layer.

In one example embodiment of the present invention, an aluminum borohydride trimethylamine (ABHTMA) precursor may be introduced onto the substrate 100 including the barrier metal layer 130 thereon as an organic aluminum precursor. The ABHTMA precursor includes aluminum as a central metal, and borohydride and trimethylamine as ligands. The ABHTMA precursor may have a higher evaporability than that of a methyl pirolidine alane (MPA) precursor used for a conventional organic aluminum precursor. When the ABHTMA precursor is introduced into a chamber for forming an aluminum wire, the organic aluminum precursor may not be thermally decomposed in advance because the ABHTMA precursor may be thermally stable at a room temperature. Thus, the generation of aluminum particles may be prevented or reduced.

The ABHTMA precursor may be introduced into the chamber in a gas phase by a liquid delivery system (LDS), a bubbling system, etc. In addition, the ABHTMA precursor may be introduced into the chamber in a vapor phase with a carrier gas. Examples of the carrier gas may include, for example, an inert gas such as an argon (Ar) gas, a helium (He) gas, a nitrogen ($N_2$) gas, or a neon (Ne) gas. These can be used individually or in a mixture of two or more thereof.

The ABHTMA precursor introduced onto the substrate 100 is thermally decomposed. The ligands are removed from aluminum of the ABHTMA precursor by a thermal decomposition to generate an aluminum atom.

Aluminum decomposed from the organic aluminum precursor is continuously chemisorbed on the barrier metal layer 130. A first aluminum layer 140 is formed on the barrier metal layer 130 by the chemisorbing aluminum.

The first aluminum layer 140 may serve as a seed layer which may improve a fluidity of a metal to be deposited in a subsequent process, and may allow the metal more easily flow into the opening 122. In addition, the first aluminum layer 140 as a seed layer may improve an adhesive characteristic of the metal.

The first aluminum layer 140 may be formed to have a substantially uniform thickness on the surface of the barrier metal layer 130. When a thickness of the first aluminum layer 140 is not uniform, the metal may not properly flow and then a void may be generated.

The first aluminum layer 140 may have a very thin thickness so as to not fill up the opening 122 having a small diameter. Thus, the first aluminum layer 140 may be formed by a process using a material favorable to step coverage. Additionally, the first aluminum layer 140 may be formed at a relatively low temperature to prevent or reduce thermal stress related damage to conductive structures located below the first aluminum layer 140.

The first aluminum layer 140 may be formed by a CVD process or a cyclic CVD process to satisfy the above properties. The first aluminum layer 140 may be formed to have a thickness of about 100 Å to about 700 Å, and preferably a thickness of about 200 Å to about 500 Å. When the first aluminum layer 140 is formed to have a thickness of about 100 Å to about 700 Å, the first aluminum layer 140 may improve a fluidity of a metal to be deposited in a subsequent process and may not completely fill the opening 122.

Figure 6:
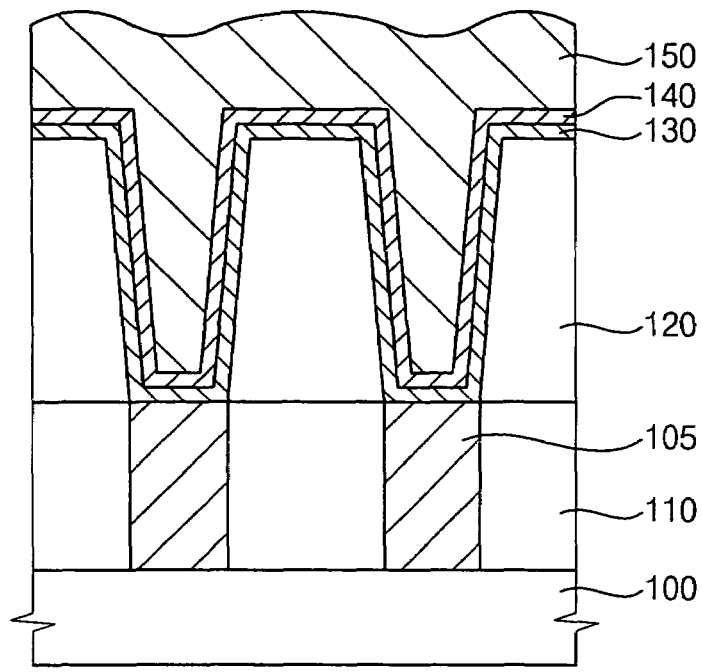

FIG. 6 is a cross-sectional view for describing a process of forming a second aluminum layer that fills the opening 122.

Referring to FIG. 6, a preliminary second aluminum layer is formed on the first aluminum layer 140 to fill the opening 122. The preliminary second aluminum layer may be formed by a physical vapor deposition (PVD) process. The PVD process may include a direct current sputtering process, an alternating current sputtering process, a direct current magnetron sputtering process, etc. For example, the preliminary second aluminum layer is formed by a direct current sputtering process.

A heat treatment is performed on the preliminary second aluminum layer at a temperature of about 350° C. to about 550° C. for a few seconds to hundreds of seconds to let the preliminary second aluminum layer reflow. A reflow process may be performed under a vacuum atmosphere to prevent an oxidation of the preliminary second aluminum layer. A second aluminum layer 150 is formed by the reflow process.

The second aluminum layer 150 may fill the opening 122 without a void and have a planarized surface. Because an oxide layer possibly disturbing a reflow of the preliminary second aluminum layer may not be formed on the first aluminum layer 140, the opening 122 may be filled up with the second aluminum layer 150 without any voids.

In one example embodiment of the present invention, an aluminum wire that may have one orientation and good electrical conductivity may be formed without particles.

Evaluation of Characteristics of an Organic Aluminum Precursor

Figure 7:
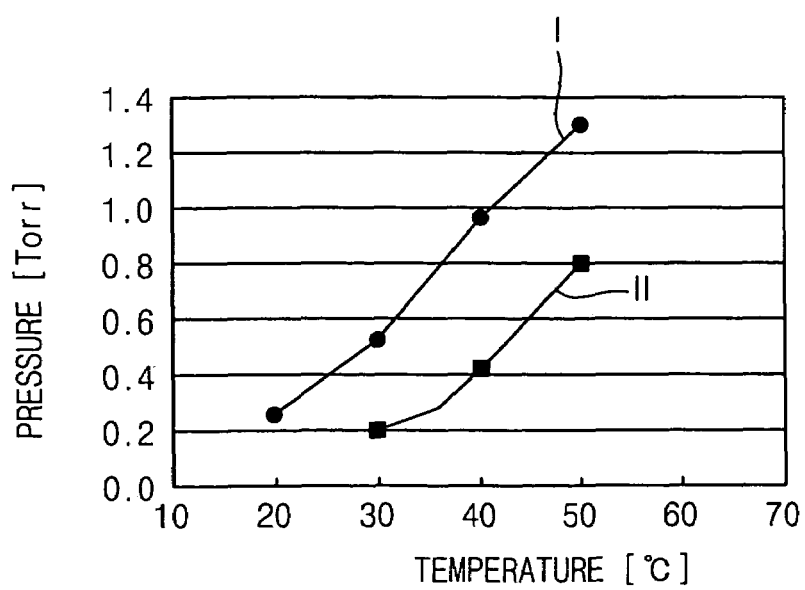
FIG. 7 is a graph illustrating changes in a vapor pressure relative to changes in temperature of an organic aluminum precursor of an example embodiment of the present invention and a conventional organic aluminum precursor.

FIG. 7 is a graph illustrating changes in a vapor pressure relative to a change in temperature of an organic aluminum precursor of embodiments of the present invention and a conventional organic aluminum precursor.

An aluminum borohydride trimethylamine (ABHTMA) precursor of embodiments of the present invention and a methyl pirolidine alane (MPA) precursor were each introduced into a container having a predetermined volume. A temperature of the each container was increased at a rate of about 5° C. per minute. A vapor pressure of the each container was measured relative to the temperature of the container. In FIG. 7, "I" illustrates a change in a vapor pressure of the ABHTMA precursor. "II" illustrates a change in a vapor pressure of the MPA precursor.

Referring to FIG. 7, a temperature of an ABHTMA precursor rises to about 50° C. with a rate of about 5° C. per minute. Then, the ABHTMA precursor has a vapor pressure of about 0.25 Torr at a temperature of about 20° C., about 0.55 Torr at a temperature of about 30° C., about 0.97 Torr at a temperature of about 40° C. and about 1.3 Torr a temperature of about 50° C. However, an MPA precursor has a vapor pressure of about 0.2 Torr at a temperature of about 30° C., about 0.42 Torr at a temperature of about 40° C. and about 0.8 Torr at a temperature of about 50° C.

As a result, the organic aluminum precursor of embodiments of the present invention has a vapor pressure twice that or even higher than that of the MPA precursor at a same temperature. That is, the organic aluminum precursor of embodiments of the present invention may be vaporized at a lower temperature than that of the MPA precursor. Thus, the organic aluminum precursor of embodiments of the present invention may exhibit improved evaporation characteristics.

Figure 8:
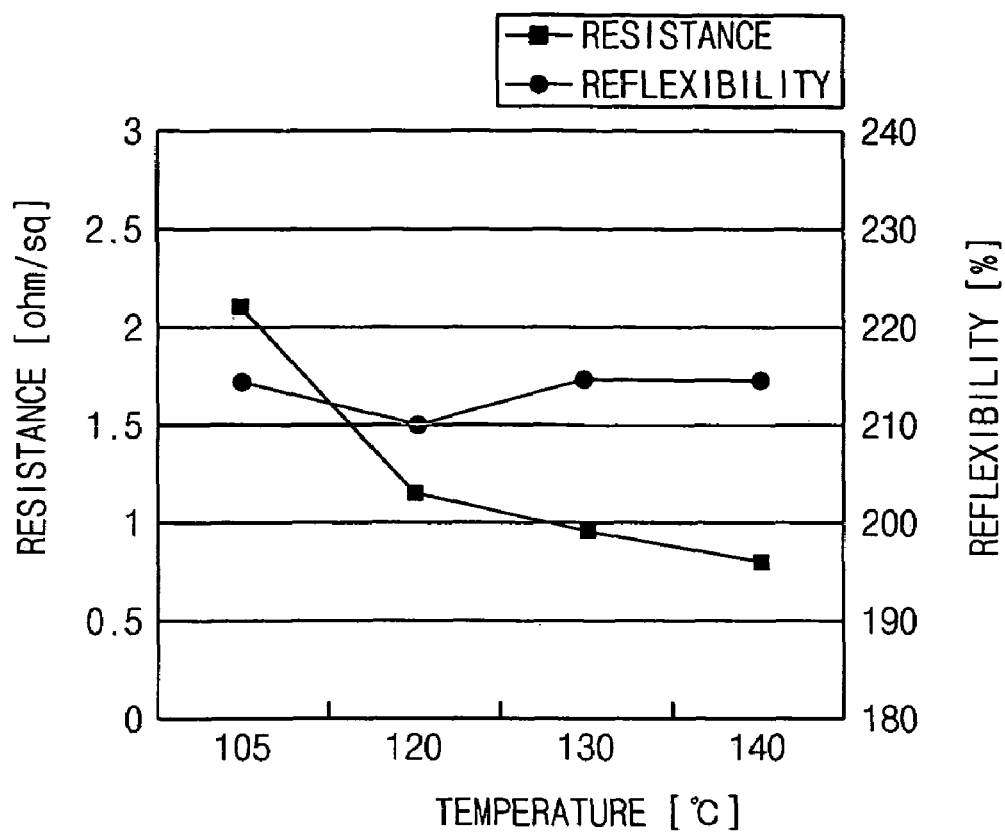
FIG. 8 is a graph illustrating a resistance and a reflexibility relative to a susceptor temperature of an aluminum layer in accordance with an example embodiment of the present invention.

FIG. 8 is a graph illustrating an electric resistance and a reflexibility of an aluminum layer relative to temperature of a susceptor of an aluminum layer formed according to embodiments of the present invention.

Referring to FIG. 8, an aluminum layer was formed on a substrate using an ABHTMA precursor sustaining a temperature of about 25° C. while a temperature of a susceptor applying heat to the substrate was varied. An electric resistance and a reflexibility of the aluminum layer were measured relative to the temperature of the susceptor. As can be seen by the results of FIG. 8, the susceptor may advantageously have a temperature of about 120° C. for forming the aluminum layer.

According to the present invention, in a chemical vapor deposition process using an organic metal precursor of embodiments of the present invention, the organic metal precursor may be thermally and chemically stable, thereby possibly not being decomposed at room temperature. Thus, a metal wire having an improved electrical conductivity may be formed without generating particles such as carbon particles and aluminum particles. In addition, a metal wire having a planarized surface and good step coverage may be formed.

The foregoing is illustrative of the present invention and is not to be construed as limiting thereof. Although a few example embodiments of the present invention have been described, those skilled in the art will readily appreciate that many modifications are possible in the example embodiments without materially departing from the novel teachings and advantages of the present invention. Accordingly, all such modifications are intended to be included within the scope of this invention as defined in the claims. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The present invention is defined by the following claims, with equivalents of the claims to be included therein.

What is claimed is:

1. A method of forming a metal wire comprising:

introducing an organic aluminum precursor comprising aluminum as a central metal, and borohydride and trimethylamine as ligands, onto a substrate with a carrier gas;

thermally decomposing the organic aluminum precursor at a temperature of about 120° C. to about 200° C.; and depositing aluminum that is decomposed from the organic aluminum precursor on the substrate to form a aluminum layer on the substrate.

wherein a chemical structure of the organic alumumum precursor is in accordance with the formula:

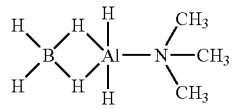

wherein the carrier gas includes at least one of an argon (Ar) gas, a helium (He) gas, a neon (Ne) gas and a nitrogen ($N_2$) gas.

2. The method of claim 1, wherein the organic aluminum precursor is vaporizes at a temperature of about 20° C. to about 50° C.

3. The method of claim 1, wherein the organic aluminum precursor has a vapor pressure of about 0.4 Torr to about 0.6 Torr at a temperature of about 30° C., and a vapor pressure of about 1.2 Torr to about 1.4 Torr at a temperature of about 50° C.

4. The method of claim 1, wherein the aluminum is deposited by a chemical vapor deposition (CVD) process or a cyclic CVD process.

5. A method of forming a metal wire comprising:
    forming an insulation layer pattern including an opening on a substrate, the opening exposing a conductive pattern formed in the substrate;
    performing a chemical vapor deposition (CVD) process or a cyclic CVD process using an organic aluminum precursor comprising aluminum as a central metal, and borohydride and trimethylamine as ligands, to form a first aluminum layer on inner walls of the opening and on an upper surface of the insulation layer pattern; and
    forming a second aluminum layer on the first aluminum layer by a physical vapor deposition (PVD) process,
    wherein a chemical structure of the organic aluminum precursor is in accordance with the formula:

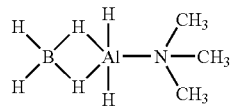

6. The method of claim 5, further comprising, after forming the insulation layer pattern and prior to forming the first aluminum layer, forming a barrier metal layer on the inner walls of the opening and on the upper surface of the insulation layer pattern.

7. The method of claim 6, wherein the barrier metal layer is formed in a single-layered structure or a multi-layered structure using at least one selected from the group consisting of titanium (Ti), titanium nitride (TiN), tantalum (Ta) and tantalum nitride (TaN).

8. The method of claim 5, wherein the CVD process or the cyclic CVD process is performed by thermally decomposing the organic aluminum precursor at a temperature of about 120 to about 200° C.

* * * * *